United States Patent
Hensel et al.

(10) Patent No.: US 12,006,282 B2
(45) Date of Patent: Jun. 11, 2024

(54) CONTINUOUS HYDROFORMYLATION PROCESS WITH CATALYST SUBSTITUTION

(71) Applicant: OQ Chemicals GmbH, Monheim am Rhein (DE)

(72) Inventors: Alexander Hensel, Essen (DE); Ruben Fernandez Diaz, Dinslaken (DE); Wolfgang Greb, Dinslaken (DE); Jörg Botterhuis, Marl (DE); Gregor Meier, Duisburg (DE)

(73) Assignee: OQ Chemicals GMBH (DE)

( * ) Notice: Subject to any disclaimer, the term of this patent is extended or adjusted under 35 U.S.C. 154(b) by 284 days.

(21) Appl. No.: 17/621,769

(22) PCT Filed: Jul. 21, 2020

(86) PCT No.: PCT/EP2020/070581
§ 371 (c)(1),
(2) Date: Dec. 22, 2021

(87) PCT Pub. No.: WO2021/013848
PCT Pub. Date: Jan. 28, 2021

(65) Prior Publication Data
US 2022/0371979 A1 Nov. 24, 2022

(30) Foreign Application Priority Data
Jul. 24, 2019 (EP) .................... 19188145

(51) Int. Cl.
*C07C 45/50* (2006.01)
*B01J 23/46* (2006.01)

(52) U.S. Cl.
CPC ............ *C07C 45/50* (2013.01); *B01J 23/464* (2013.01)

(58) Field of Classification Search
CPC .............................. C07C 45/50; B01J 23/464
See application file for complete search history.

(56) References Cited

U.S. PATENT DOCUMENTS

| | | | |
|---|---|---|---|
| 4,801,754 A | 1/1989 | Bach et al. | |
| 6,700,021 B2 * | 3/2004 | Bohnen | C07C 45/50 568/429 |
| 6,864,387 B2 | 3/2005 | Riedel et al. | |
| 7,259,279 B2 | 8/2007 | Thiel et al. | |
| 9,688,598 B2 | 6/2017 | Eisenschmid et al. | |

FOREIGN PATENT DOCUMENTS

| | | | |
|---|---|---|---|
| CN | 102617308 A | 8/2012 | |
| EP | 0269011 A1 | 6/1988 | |
| JP | S63150239 A | 6/1988 | |
| JP | 2006143725 A | 6/2006 | |
| JP | 2015516388 A | 6/2015 | |
| JP | 2016540780 A | 12/2016 | |
| WO | 2013153136 A1 | 10/2013 | |
| WO | WO-2013153136 A1 * | 10/2013 | ............ C07C 45/50 |
| WO | 201313136 A1 | 10/2017 | |

OTHER PUBLICATIONS

Written Opinion PCT/EP2020/070581, Oct. 12, 2014.
International Search Report PCT/EP2020/070581 dated Oct. 1, 2020.
Translation of International Preliminary Report on Patentability mailed Feb. 3, 2022.

* cited by examiner

*Primary Examiner* — Sikarl A Witherspoon
(74) *Attorney, Agent, or Firm* — M. Susan Spiering; Ochoa & Associates, P.C.

(57) ABSTRACT

The present invention relates to a continuous two-phase hydroformylation process for the production of aldehydes from olefins by means of carbon monoxide, hydrogen and a transition metal catalyst in a reaction zone, the transition metal being in the form of a water-soluble catalyst complex, wherein the process comprising the following steps once or several times:
a) hydroformylating by reacting the olefins, carbon monoxide and hydrogen over a water-soluble transition metal catalyst comprising water-soluble organophosphorus ligands in the reaction zone;
b) reducing the concentration of the olefins in the reaction zone by reducing the olefin feed to the reaction zone and withdrawing at least a portion of the catalyst solution from the reaction system, wherein the catalyst solution withdrawal and olefin concentration reduction substeps may occur in this or reverse order, simultaneously or sequentially;
c) feeding a solvent, a transition metal source and water-soluble organophosphorus ligands to the reaction system, wherein the feeding of the components may occur simultaneously or in any order sequentially;
d) increasing the concentration of the olefins in the reaction zone by increasing the olefin feed to the reaction zone and hydroformylating by reacting the olefins with carbon monoxide and hydrogen.

19 Claims, 1 Drawing Sheet

CONTINUOUS HYDROFORMYLATION PROCESS WITH CATALYST SUBSTITUTION

CLAIM FOR PRIORITY

This application is a National Phase Application of Application No. PCT/EP2020/070581 filed Jul. 21, 2020 which was based on Application No. EP 19 188 145.7 filed Jul. 24, 2019. The priorities of the foregoing applications is hereby claimed and their disclosures incorporated herein by reference.

TECHNICAL FIELD

The present invention relates to a continuous two-phase hydroformylation process for the production of aldehydes from olefins by means of carbon monoxide, hydrogen and a transition metal catalyst in a reaction zone, the transition metal being in the form of a water-soluble catalyst complex, the process comprising the following steps once or several times:
  a) hydroformylating by reacting the olefins, carbon monoxide and hydrogen over a water-soluble transition metal catalyst comprising water-soluble organophosphorus ligands in the reaction zone;
  b) reducing the concentration of the olefins in the reaction zone by reducing the olefin feed to the reaction zone and withdrawing at least a portion of the catalyst solution from the reaction system, wherein the catalyst solution withdrawal and olefin concentration reduction substeps may occur in this or reverse order, simultaneously or sequentially;
  c) feeding a solvent, a transition metal source and water-soluble organophosphorus ligands to the reaction system, wherein the feeding of the components may occur simultaneously or in any order sequentially;
  d) increasing the concentration of the olefins in the reaction zone by increasing the olefin feed to the reaction zone and hydroformylating by reacting the olefins with carbon monoxide and hydrogen.

BACKGROUND

Hydroformylation processes have been known for a long time in a wide variety of process designs. What they all have in common is that olefins are converted to aldehydes in the presence of hydroformylation catalysts with hydrogen and carbon monoxide, the latter usually being fed together to the reaction as synthesis gas. For example, the hydroformylation of propylene yields a mixture of straight-chain n- and branched i-butyraldehyde, of which the n-isomer is usually the economically desired product.

While in the beginning the reactions were carried out over cobalt catalysts, rhodium has meanwhile become established as advantageous. Compared to cobalt catalysis, high productivities and preferred n/i-ratios can be obtained using rhodium complex catalysts under comparatively milder reaction conditions. In addition, the solubility properties of the catalyst can be adjusted within certain limits by selecting suitable ligands, which facilitates recovery of the expensive catalyst and also influences the catalytic properties of the rhodium-ligand complex.

Due to the flexibility of the reaction, two different reaction methods have emerged for rhodium-catalyzed hydroformylations. Both differ in the way the crude product is separated from the catalyst and are referred to as liquid/liquid or steam processes.

In liquid/liquid processes, the raw product and other components, such as the catalyst, are separated by phase separation into a liquid organic phase and an aqueous phase. Both phases can be drawn off independently of each other, with the crude product, possibly with by-products, in the organic phase and the catalyst in the aqueous phase. What is advantageous about this work-up is that, due to the two-phase design, the separation operation can be carried out for a wide range of different product aldehydes, irrespective of further properties, such as the volatility of the product and possibly further by-products. Furthermore, this work-up can be carried out without a large thermal load.

In the second processing, the steam processing, the crude product is separated in the gas phase. As a function of the boiling point of the olefins used, the steam process can be carried out in two different ways. The lower aldehydes with a correspondingly low boiling point obtained from easily vaporizable olefins are usually first condensed and separated as a liquid from the remaining gaseous components, for example unreacted olefin and synthesis gas, and then subjected to thermal separation. Unreacted reactants are returned in gaseous form to the original reactor or to further downstream reactors. In this respect, the process is referred to as a gas recirculation or gascycle process. Higher olefins are mostly reacted by means of a liquid recirculation process, in which a volume of solution is continuously withdrawn from the reaction zone and fed to a single- or multi-stage evaporation. The resulting separated catalyst solution can then be fed back into the reactor.

As a function of the olefin feedstocks, the apparatus set-up and the selected reaction conditions, there are thus a wide range of process engineering combination options, which require different process parameters and catalyst systems. However, all process designs have in common that the catalyst used ages over time under the reaction conditions or as a result of the work-up operations. As a result, the yields decrease and/or the achievable isomer ratio shifts unfavourably. Although the consequences of aging can be partially compensated for by adjusting the reaction conditions, for example by increasing the temperature in the reaction zone, ultimately the reaction has to be terminated and the spent catalyst reprocessed within regular time intervals in order to maintain an economical reaction.

In the patent literature there are some proposals for a continuous process control, which should enable high yields over long periods of time.

For example, EP 2 417 093 B1 discloses a process in which the waste gas resulting from the hydroformylation of unsaturated compounds in the presence of an aqueous catalyst solution containing water-soluble rhodium complex compounds (first reaction stage) is fed to a homogeneous reaction system in which the residual amounts of the olefinically unsaturated compounds from the first reaction stage are reacted with organic phosphorus (III) compounds in the presence of complex compounds of rhodium (second reaction stage). The discharge from the second reaction stage is first degassed and then passed through two flash stages to form waste gas. The resulting liquid phase is distilled, the rhodium-containing residue obtained being partly discharged and partly recycled to the second reaction stage with the addition of fresh rhodium and fresh organic phosphorus (III) compounds. Moreover, this step discloses that the activity obtained is lower after addition of fresh rhodium and this is probably due to catalytically inactive metal.

EP 2 836 474 B1 discloses a process for continuous hydroformylation in which an olefin feedstock containing at least one olefin having from 3 to 20 carbon atoms is reacted at elevated temperature and pressure in a reaction zone with synthesis gas in the presence of a homogeneous transition metal catalyst complexed with an organophosphorus ligand and free ligand, wherein the catalyst is formed in situ in the reaction zone and a solution of a transition metal source is added to the reaction zone to compensate for catalyst losses, characterized in that the space-time yield of the reaction zone of hydroformylation product is continuously determined and the rate of addition of the transition metal source to the reaction zone is controlled as a function of the space-time yield, wherein an adjusting means is provided for adjusting the rate of addition of the transition metal source into the reaction zone, a target value for the space-time yield of hydroformylation product of the reaction zone is determined, the actual value for the space-time yield is determined, after a lower limit value for the deviation of the actual value from the target value is reached, the amount of transition metal source required to control the catalyst loss is determined and adding a solution of the transition metal source to the reaction zone, the rate of addition of the transition metal source to the reaction zone being controlled so that the space-time yield does not exceed an upper limit for the deviation of the actual value from the target value.

Another way to increase the efficiency of the catalyst system is disclosed in EP 0 246 475 A1. This document teaches a process for the preparation of aldehydes by reacting unsaturated compounds with carbon monoxide and hydrogen at temperatures of 20 to 150° C. and pressures of 0.1 to 20 MPa in the liquid phase in the presence of water and a water-soluble, rhodium-containing complex compound as catalyst, the rhodium complex compound being prepared from the rhodium salt of a carboxylic acid having 2 to 4 carbon atoms dissolved in an aliphatic, cycloaliphatic or aromatic hydrocarbon before the onset of the hydroformylation reaction, cycloaliphatic or aromatic hydrocarbon by reaction with carbon monoxide and hydrogen at pressures of 0.1 to 1.8 MPa and temperatures of 50 to 100° C., the preforming being carried out in the presence of said aqueous solution of a water-soluble triarylphosphine or said aqueous solution being added after the preforming of the previously prepared rhodium complex compound.

Thus, a wide variety of processes are known from the literature in which further partial amounts of catalyst are added to the reaction zone of a homogeneous hydroformylation process of whatever design, either a reprocessed catalyst previously removed from the reaction zone, a fresh catalyst or a combination of both types of catalyst. However, for a two-phase hydroformylation process, such as the Ruhrchemie/Rhone-Poulenc process, no corresponding method for removing and adding a partial amount of catalyst has been possible so far. Thus, there is a great interest in continuous large-scale process designs for hydroformylations, which are able to deliver consistently high selectivities and high product yields over longer periods of time.

SUMMARY OF INVENTION

It is therefore the object of the present invention to provide an improved continuous hydroformylation process which at least partially counteracts the disadvantages of the prior art.

A method according to claim 1 is therefore proposed for solving this problem. Preferred embodiments of the method according to the invention are given in the dependent claims.

In accordance with the invention, the problem is solved by a continuous two-phase hydroformylation process for the preparation of aldehydes from olefins by means of carbon monoxide, hydrogen and a transition metal catalyst in a reaction zone, the transition metal being in the form of a water-soluble catalyst complex, the process comprising the following steps once or several times:

a) hydroformylating by reacting the olefins, carbon monoxide and hydrogen over a water-soluble transition metal catalyst comprising water-soluble organophosphorus ligands in the reaction zone;

b) reducing the concentration of the olefins in the reaction zone by reducing the olefin feed to the reaction zone and withdrawing at least a portion of the catalyst solution from the reaction system, wherein the catalyst solution withdrawal and olefin concentration reduction substeps may occur in this or reverse order, simultaneously or sequentially;

c) feeding a solvent, a transition metal source and water-soluble organophosphorus ligands to the reaction system, wherein the feeding of the components may occur simultaneously or in any order sequentially;

d) increasing the concentration of the olefins in the reaction zone by increasing the olefin feed to the reaction zone and hydroformylating by reacting the olefins with carbon monoxide and hydrogen.

Surprisingly, it has been found that by means of the above-mentioned process steps, continuous hydroformylations according to the Ruhrchemie/Rhone-Poulenc process can be performed almost indefinitely without the need to terminate the entire process due to catalyst ageing and to remove the catalyst in its entirety from the reaction zone and reprocess it. High productivities and high selectivities can be achieved over long periods of time with very little intervention in the hydroformylation process as such, and the overall process can also advantageously be run with less catalyst and ligand input compared to standard prior art processes. It is possible to obtain active catalysts with high efficiency directly in the reaction zone. The catalytically active complexes formed from metal and ligand are in equilibrium with each other, which can be shifted to more active as well as selective complexes depending on the chemical environment and the physical boundary conditions. In this respect, for the central atom of the catalytic complexes under the reaction conditions of the reaction zone, the ligands are usually exchanged in the ligand sphere. The coordination of the potential ligands at the metal center thereby determines the catalytic activity and in particular also the induced regioselectivity and thus ultimately the obtainable isomer ratio in the crude product. The formation of the complexes is thereby influenced not only by the ligands used to build up the desired catalyst, i.e. hydrogen, carbon monoxide, olefin and organophosphorus ligand, but also by further degradation and by-products present in the reaction zone, which can contribute to undesirable properties and to a deterioration of the synthesis performance through their incorporation into the ligand sphere of the metal complexes. In this respect, it has not been foreseeable that conversion to a highly efficient catalyst would succeed in such a reaction zone environment. Without being bound by theory, the fact that a highly efficient catalyst is obtained is attributed to a synergistic interaction of at least two causes. First, the addition of new catalyst metal occurs in the absence of the olefin in the reaction zone, and second, the catalyst solution in the reaction zone, diluted by the degradation and by-products, appears to be conducive to the formation of highly selective and efficient catalyst complexes. This theory is supported by the fact that supplements of the catalyst metal in the presence of the olefin and to an undiluted solution do not lead to any appreciable increase in activity or improvement in n/i selectivity. Usually, in order to extend the catalyst lifetimes in the continuous hydroformylation processes considered here, only further organophosphorus ligands are added, which are intended to displace the catalyst poisons present in the metal complexes, such as ligand degradation products, as part of an equilibrium reaction and thus to convert the catalyst back into a more active form. However, the latter maintenance measures require high amounts of ligands and ultimately cannot prevent a termination of the continuous reaction and an overall replacement of the catalyst, since the decomposition of the ligands present continuously increases the concentration of catalyst poisons. The catalysts returned to the reaction zone by recirculation processes also do not seem suitable for the formation of similarly efficient catalyst complexes, despite additional supplementation of fresh catalyst metal, probably based on a different chemical environment and/or due to the nevertheless different volume flow rates.

BRIEF DESCRIPTION OF DRAWINGS

The invention is described in detail below with reference to the drawings, wherein.

DETAILED DESCRIPTION

The process according to the invention relates to a continuous two-phase hydroformylation process. In the process according to the invention, the active catalyst metal is present in an aqueous phase and the organic aldehydes formed, together with any organic by-products formed, are present in an organic phase formed from them. The reaction of the olefins takes place in a two-phase system of organic and aqueous phases. The active metal complex is in turn homogeneously dissolved in the aqueous phase. The process is a continuous process, since to carry out the actual reaction the reactants are continuously fed into the reaction zone and the products formed are continuously removed from it.

By means of the process according to the invention, aldehydes are prepared from olefins. By way of example, the conversion can be illustrated by the conversion of propene:

Both the straight-chain n- and branched i-aldehyde are obtained from the hydroformylation. The olefines that can be used may be linear or branched and may have a terminal or internal double bond. Examples of such olefines are: ethylene, propylene, 1-butene, 2-butene, 1-pentene, 2-methyl-1-butene, 1-hexene, 1-heptene, 1-octene, 4,4-dimethyl-1-nonene, 1-dodecene. Preferably, linear olefines with 2 to 8 carbon atoms such as ethylene, propylene, 1-butene, 1-pentene, 1-hexene, 1-heptene and 1-octene or mixtures of at least two possible double bond isomers thereof may be used.

The reaction of the olefins takes place in the presence of carbon monoxide and hydrogen. Usually, these reactants are used together as synthesis gas. The total pressure of hydrogen and carbon monoxide can be 1-200 bar ($100\text{-}2*10^4$ kPa), preferably 10 to 100 bar ($1*10^3$ to $1*10^4$ kPa). The composition of the synthesis gas, i.e. the ratio of carbon monoxide to hydrogen, can be varied within wide limits. Generally, synthesis gas is used in which the volume ratio of carbon monoxide to hydrogen is 1:1 or deviates only slightly from this value.

A transition metal catalyst is used for the reaction, wherein the transition metal catalyst is in the form of a water-soluble catalyst complex. Transition metals which can be used are, for example, the transition metals of the $8^{th}\text{-}10^{th}$ subgroup, such as, for example, cobalt, rhodium, iridium, iron, ruthenium, osmium and platinum. Preferably, cobalt or rhodium may be used, of which rhodium is particularly preferred. The reaction and catalysis take place in the aqueous phase and requires the metal complexes to be soluble in water. Typically, the catalyst is assumed to be present in the aqueous phase coordinated both with the reactants as ligands and with the water-soluble organophosphorus ligands, the latter in particular contributing to the water solubility of the complex. However, in the course of hydroformylation and as a function of the chemical environment, the ligand sphere may change, for example by incorporation of hydrogen, olefin or carbon monoxide, so that it is assumed that catalyst complexes with mixed and different ligand spheres may be present, these complexes still ultimately being water-soluble.

The process according to the invention may comprise one or more of the claimed steps. Preferably, the process may be carried out more frequently in order to extend the catalyst life and thus the overall process duration. For example, it is possible to perform the process as a function of the current synthesis rate, the measured isomer ratio, or alternatively as a function of the salt load of the aqueous catalyst solution. For example, the process may be carried out 1-100 times, preferably 1-50 times, further preferably 1-10 times. In particular, according to the invention it is not envisaged that the process is carried out continuously, i.e. continuously in the course of a hydroformylation. This means that carrying out a pure recirculation process with continuous separation and/or preparation of the catalyst is not to be included under the process according to the invention.

In process step a), hydroformylation is carried out by reacting the olefins with carbon monoxide and hydrogen over a water-soluble transition metal catalyst comprising water-soluble organophosphorus ligands in the reaction zone. In this process step, the catalytic conversion of the reactant olefins to the desired aldehydes occurs. The reaction usually takes place in a reactor into which the reactants are fed in gaseous form. Within the reactor, the catalyst is present dissolved in a liquid aqueous phase through which the gaseous reactants flow and are saturated. According to the invention, this location in the reactor forms the reaction zone.

The term water-soluble organophosphorus ligands can be understood to mean, for example, compounds from the class of triarylphosphines and diphosphines which are soluble in water due to the presence of one or more sulfonate or carboxylate groups in the molecule. The water-soluble triaryl-, in particular triphenylphosphines follow the general formula (I), (I)

wherein $Ar^1$, $Ar^2$, $Ar^3$ each independently represent a phenyl or naphthyl group, $Y^1$, $Y^2$, $Y^3$ each independently represent a straight-chain or branched alkyl group having 1 to 8 C atoms, a straight-chain or branched alkoxy group having 1 to 8 C atoms, a halogen atom, an OH, CN, $NO_2$ or $NR^1R^2$ group, wherein $R^1$ and $R^2$ each represent a straight-chain or branched alkyl group having 1 to 8 C atoms, $X^1$, $X^2$, $X^3$ independently of one another represent a carboxylate ($COO^-$—) and/or a sulphonate ($SO_3^-$) radical, $m_1$, $m_2$, $m_3$ are identical or different numbers from 0 to 3, at least one number $m_1$, $m_2$, $m_3$ being equal to or greater than 1, and $n_1$, $n_2$, $n_3$ are identical or different integers from 0 to 5. The negative charge of $X^1$, $X^2$, $X^3$ is neutralized by counterions, for example alkali metal ions, alkaline earth metal or zinc ions, ammonium or quaternary ammonium ions. Preferred are water-soluble triarylphosphines of the general formula described above, in which Ar is each a phenyl radical and the X is each a sulfonate radical or a carboxylate radical. Examples of this class of compounds of the general formula reproduced above are triphenylphosphine tri-sodium trisulfonate (TPPTS), triphenylphosphine tri-(tetraalkylammonium) trisulfonate, triphenylphosphine tri-sodium tricarboxylate. The sulfonated or carboxylated aryl phosphines can be used as pure compounds. However, mixtures of phosphines bearing different numbers of sulfonate or carboxylate groups may also be used. Particularly preferably, triphenylphosphine tri-sodium trisulfonate according to formula (II) can be used as the water-soluble organophosphorus complex ligand:

(II)

TPPTS

Sulfonated diphosphines of the general formulae (III) and (IV) are also suitable as water-soluble diphosphines.

In (III), each $n_4$ and $n_5$ independently represents 0 or 1, and the compound of formula (III) may contain up to six —$SO_3M$ groups.

In (IV), each $n_6$, $n_7$, $n_8$ and $n_9$ are independently 0 or 1, wherein the compound of formula (IV) contains from four to eight —$SO_3M$ groups.

In formulae (III) and (IV), M represents ammonium, a monovalent metal or the equivalent of a polyvalent metal, in particular sodium, potassium, calcium or barium.

In process step b), the concentration of the olefins in the reaction zone is reduced by reducing the olefin feed to the reaction zone and at least a portion of the catalyst solution is removed from the reaction system, wherein the substeps of removing the catalyst solution and reducing the olefin concentration may be performed in this or reverse order, simultaneously or sequentially. The concentration of the olefins may be achieved, for example, by stopping the feed and reacting off the compounds still in the reactor. More conveniently, the molar concentration of the olefins in this step is brought to 10%, preferably 5%, more preferably less than 1%, relative to the olefin concentration prevailing in process step a). A partial amount of catalyst solution comprises a significant portion of catalyst solution which is larger than the portion which is discharged from the reaction zone, for example in continuous circulation processes. The partial amount may comprise a volume greater than 5%, preferably greater than 10%, more preferably greater than 15%, and further preferably greater than 20% of the total aqueous catalyst solution. This process step may be initiated, for example, by draining the catalyst solution. Subsequently, the olefin concentration may then be reduced. Preferably, however, the draining of the catalyst solution may occur after the reduction of the olefin concentration.

The reaction system is formed by the reaction zone in the reactor and, if necessary, further equipment such as the catalyst circulation flow. Thus, the catalyst does not necessarily have to be withdrawn directly from the reaction site. It is possible that the catalyst is circulated and the removal of the catalyst is carried out at another point in the circuit. This measure also inevitably leads to a reduction in the amount of catalyst in the reaction zone.

In process step c), a solvent, a transition metal source and water-soluble organophosphorus ligands are fed to the reaction system, whereby the components can be fed simultaneously or in any order one after the other. Thus, the volume of catalyst removed may be replaced in part, in whole or in excess by a solvent, for example water. To the now diluted catalyst solution in the reaction zone can then be added the transition metal source, followed by the water-soluble organophosphorus ligand. The latter additions may, for example, be in the form of concentrated aqueous solutions with some of the solvent. However, it is also possible to feed all components, solvent, transition metal source and complex ligand as one solution to the reaction system. The components may be combined in the reaction zone or in the reaction system. Furthermore, it is also possible to supply the complex ligand, at least partially, already as part of the transition metal source. This means that, for example, a preformed catalyst complex with water-soluble organophosphorus complex ligands can already be used as a transition metal source. Possible non-preformed, water-soluble transition metal sources are, for example, rhodium sources such as, for example, $[Rh(octanoate)_2]_2$, $[Rh(acac)(CO)_2]$, $[Rh(2-ethylhexanoate)_3]$, $[Rh(2-ethylhexanoate)_2]_2$, $[Rh(acac)(cod)]$, $[Rh(cod)Cl]_2$, $[Rh(acac)_3]$, $[Rh(cod)_2]BF_4$, $[Rh(OAc)_3]$ or mixtures thereof. After feeding the components, the new catalyst solution can be preformed under synthesis gas for a certain time, converting the transition metal source into the active catalyst under the applied chemical and physical conditions and in the presence of the corresponding water-soluble organophosphorus ligands.

In process step d), the concentration of the olefins in the reaction zone is then increased by increasing the olefin feed to the reaction zone and hydroformylation by reacting the olefins with carbon monoxide and hydrogen. In this regard, the increase in olefin concentration in the reaction zone may be accomplished by starting the feed of the gaseous olefin.

Expediently, the olefin concentration can be increased to the value as it was in process step a). However, it is also possible to feed a higher olefin concentration due to the increased catalyst activity. By feeding the olefin to the reaction zone again, metal-catalyzed aldehydes are formed again by means of the synthesis gas.

In a preferred embodiment of the process, in process step b) the sub-step of reducing the olefin concentration may take place before the partial withdrawal of the catalyst solution. It has been found to be particularly advantageous for the interruption times of the hydroformylation that the reduction of the olefin concentration takes place before the partial withdrawal of the catalyst solution. Since in this embodiment a larger catalyst concentration is present, the olefin concentration can be reduced more rapidly compared to an embodiment in which a portion of the catalyst solution would already have been removed. Advantageously, in this embodiment, less olefin is discharged with the partial catalyst solution.

In a preferred embodiment of the process, in process step b) the molar olefin concentration in the reaction zone can be reduced by greater than or equal to 50% and less than or equal to 100% relative to the olefin concentration in the reaction zone in process step a). In order to obtain a catalyst which is as active as possible after the partial substitution of the catalyst solution, it has been found to be particularly advantageous that the olefin content in the reaction zone is significantly reduced. Particularly preferably, the substitution may be carried out entirely in the absence of olefins in the reaction zone. This can lead to particularly active and selective catalysts in the reaction zone after substitution, which improves the economy of the entire process. GC methods can be used to determine the concentration of olefins still present in the reaction zone.

Within a preferred aspect of the process, a volume greater than or equal to 10% and less than or equal to 50% of aqueous catalyst solution may be withdrawn from the reaction system in process step b). In order to obtain the most economical process possible, partial withdrawal volumes indicated above have been found to be particularly suitable. Smaller withdrawal quantities can lead to an insufficient restoration of the catalyst activity and higher withdrawal quantities to an excessive disturbance of the equilibrium in the reaction zone. Preferably, the partial withdrawal volume may further be $\geq 15\%$ and $\leq 45\%$, further preferably $\geq 20\%$ and $\leq 40\%$.

In a further embodiment of the process, the volume of liquid components added in process step c) may be greater than or equal to 20% and less than or equal to 200% relative to the catalyst solution removed in process step b). To obtain a very active reactivated catalyst solution with a relatively low content of interfering catalyst poisons, it has been found to be particularly suitable that the volume of the partial removal amount removed from the reaction zone is approximately balanced by the volume of the newly added components. Further dilution by addition of a larger volume, as indicated above, is usually harmless within the limits indicated and may contribute to a further reduction in the salinity or organic components in the aqueous catalyst solution. Moreover, these added volumes may be further actuating components with which to respond to the increased efficiency of the catalyst solution. Lower volumes may be disadvantageous as this may result in insufficient dilution of the total catalyst phase in the reaction zone.

In a further embodiment of the process, in process step c), rhodium compounds selected from the group of rhodium (III) salts such as Rh-2-ethylhexanoate, -acetate, -oxalate, -propionate, -malonate, $Rh(NO_3)_3$, $Rh(SO_4)_3$, $RhCl_3$ or the rhodium complex compounds such as cyclopentadienylrhodium compounds, $[RhCl(cyclooctadiene-1,5)]_2$, rhodium acetylacetonate, the rhodium carbonyl compounds such as $Rh_3(CO)_{12}$, $Rh_6(CO)_{16}$ or in the form of the various rhodium oxides or mixtures of at least two compounds thereof. This group of Rh compounds has been found to be a particularly suitable source of rhodium. These compounds can be rapidly converted to the desired active catalyst species under the physical and chemical conditions of the reaction system or reaction zone, and provide high productivities and selectivities after short preforming times. This can contribute to an increase in the economics and lifetime of the process. In particular, the use of these rhodium sources can eliminate the need for further setups to preform the catalyst, since the formation of the catalyst, i.e. the conversion to the active catalyst with hydrogen, carbon monoxide and water-soluble organophosphorus complex ligands, takes place in the reaction zone itself.

In another preferred aspect of the process, preformed rhodium complexes with organophosphorus ligands may be added to the reaction system as a transition metal source in process step c). In order to shorten the preforming time of the catalyst in the reaction zone, it has been found to be advantageous to supply already preformed catalysts to the reaction zone as the rhodium source. In this zone, a faster equilibration and adaptation to the reaction conditions takes place. In this way, very short interruptions of the synthesis for the substitution of the catalyst solution can be ensured.

Within a further embodiment of the process, organophosphorus ligands may be added in process step c) in a molar ratio of greater than or equal to 20 and less than or equal to 400 relative to the amount of transition metal removed in process step b). The addition of ligands indicated above has been found to be particularly suitable for the rapid setting of the complete catalyst in the reaction zone which is as active as possible. This amount can contribute to a particularly rapid preformation of the rhodium-phosphine complexes newly formed by the addition of organophosphorus ligands and, moreover, to a reactivation of the catalysts remaining in the reaction zone. The latter may have been impaired in their synthetic performance and/or selectivity by catalyst poisons. Higher ratios can lead to an excessive organic/salt loading of the aqueous phase and lower ratios to an insufficient reactivation of the catalyst metal centres.

Within a preferred embodiment of the process, a solution of a rhodium compound comprising organophosphorus ligands can be added to the reaction system in process step c). To simplify the addition steps and for rapid equilibrium adjustment, a simultaneous addition of a non-preformed solution of a rhodium compound which also comprises water-soluble organophosphorus ligands has proved to be particularly suitable. This process control eliminates the need for further technical setups to achieve preformation of the catalyst. Furthermore, the preforming in the reaction zone can be faster compared to a separate addition of the components. Preferably, the addition can also be made directly to the reaction zone.

In a preferred aspect of the process, organophosphorus ligands may be added to the reaction system in process step c) prior to addition of the transition metal source. If the catalyst solution already exhibits a high degree of aging, such as an unfavourably altered/deteriorated isomeric ratio or very insufficient activity, it may prove advantageous to first contact the residual amount of catalyst solution remaining in the reaction zone with a water-soluble organophosphorus ligand before adding the fresh transition metal source. This process control can contribute to a more selective activation of the remaining catalyst and, compared to a simultaneous addition of transition metal source and organophosphorus ligand, a more active and selective catalyst is obtained in the reaction zone in total. The organophosphorus ligands can be added directly to the reaction zone or, for example, via addition to the catalyst circuit in the reaction system.

According to a further, preferred embodiment of the process, in process step c) first a partial amount of the solvent, then the transition metal source dissolved in a solvent and then the organophosphorus ligands can be added to the reaction system. It has been found to be particularly suitable for controlled reaction control that the addition in this process step proceeds in the order indicated above. By sequential addition, a dilute aqueous catalyst solution can always be obtained first in the reaction zone, to which the further components are then added. By suitable technical measures or by syngas convection of the solution in the reaction zone, the equilibration can furthermore be accelerated.

According to a preferred characteristic of the process, the process steps b) and c) can reduce the total concentration of organic ligands and salts present in the aqueous solution of the reaction zone by greater than or equal to 10% and less than or equal to 50% compared to the concentration of organic ligands and salts in the aqueous solution of the reaction zone at the end of the process step a). Surprisingly, it has been shown that the process according to the invention is able to significantly reduce the salt content and/or the organic load in the aqueous catalyst solution of the reaction zone. In particular, the concentration of ligand degradation products can be reduced, thereby increasing the overall longevity of the catalyst in the reaction zone. The amount of organophosphorus ligands in the aqueous solution can be determined, for example, via HPLC measurements. In particular, the amount of TPPTS degradation products can be reduced, which leads to an improvement in the isomer ratio. In this context, the organic ligands include, in particular, complexing agents having a carbon skeleton and heteroatoms, the complex formation proceeding via the heteroatoms. Thus, the organic ligands include the desired functional organophosphorus ligands and their degradation products. In addition, the group of organic ligands also includes the ligands of the water-soluble, added transition metal sources, for example in the form of acetate or similar compounds with carbon and heteroatom moieties.

Within a further embodiment of the process, in process step c), the pH in the aqueous solution of the reaction zone can be adjusted to a range of greater than or equal to pH 4 and less than or equal to pH 10 after addition of the components. To obtain the highest possible catalyst activity, it has also been found useful to adjust the pH of the catalyst solution in the reaction zone after the addition sequence. This can be done by known adjusting agents such as inorganic acids or bases. It is also possible to already provide the newly added amount of catalyst with these and thus achieve an acceleration of the process/reactivation times. In a further preferred embodiment, the pH can be adjusted between greater than or equal to pH 5 and less than or equal to pH 8, further preferably between greater than or equal to pH 5.5 and less than or equal to pH 7.

In a further embodiment of the process, the molar ratio of organophosphorus ligands added to transition metal added in process step c) may be greater than or equal to 20 and less than or equal to 500. In order to stabilize the transition metal source and to accelerate the equilibration, it has been found to be beneficial to use the water-soluble organophosphorus ligand in a high excess in this step. Preferred ratios are further between greater than or equal to 120 and less than or equal to 450, and preferably greater than or equal to 150 and less than or equal to 400.

According to a further preferred embodiment of the process, the concentration of inorganic cations in the solution of the reaction zone can be reduced by greater than or equal to 5% by means of the process steps b) and c). It has also been found to be highly advantageous that in addition to reducing the concentration of organic ligands in the reaction zone, the amount of inorganic cations is also reduced. Inorganic cations include, for example, alkali and alkaline earth ions. Without being bound by theory, these ions can apparently either be part of the catalyst complexes or contribute to improving the solubility of the olefins into the aqueous phase by changing the distribution equilibrium of the olefin between the aqueous and organic phases. Thus, by reducing the concentration of the cations, the polarity of the aqueous phase is lowered and a more advantageous phase equilibrium for the olefin can be achieved. The latter may in particular contribute to an increase in the reaction rate. In particularly preferred embodiments, the concentration of inorganic cations in the reaction zone solution may be reduced by greater than or equal to 10%, more preferably by greater than or equal to 15%. These ranges of cation reduction may contribute to a particularly efficient recovery of catalyst activity. The measurement of the concentrations may be carried out, for example, by ICP methods.

Figure 1:
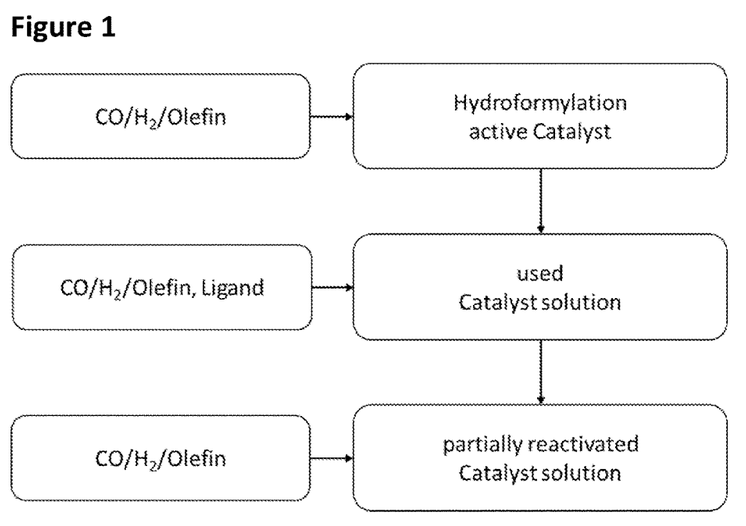
FIG. 1 is a schematic representation of the process sequence of a continuous Ruhrchemie/Rhone-Poulenc hydroformylation process.
Figure 2:
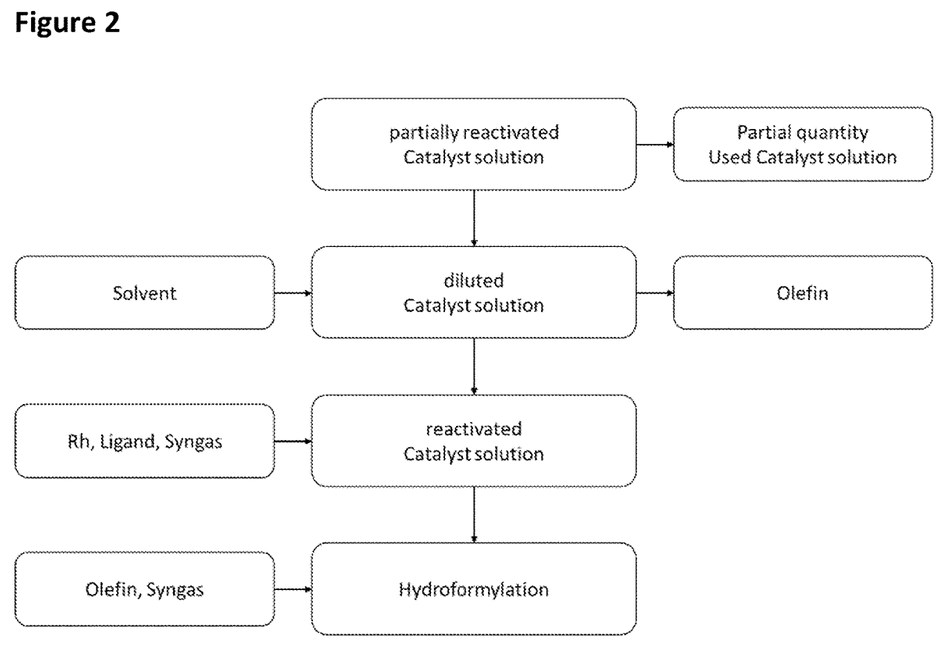
FIG. 2 is a schematic representation of the process sequence when carrying out the hydroformylation process according to the invention.

Further details, features and advantages of the subject matter of the invention will be apparent from the dependent claims and from the following description of the figures and associated examples. It shows the:

FIG. 1 in a schematic way the process sequence of a continuous Ruhrchemie/Rhone-Poulenc hydroformylation process;

FIG. 2 schematically the process sequence when carrying out the hydroformylation process according to the invention.

FIG. 1 schematically shows the performance of a continuous Ruhrchemie/Rhone-Poulenc hydroformylation process. To an aqueous, active catalyst solution in a reaction zone, the olefin starting material and synthesis gas are continuously fed. The applied reaction conditions cause chemical degradation of the catalyst, resulting in deterioration of the synthesis performance and selectivity of the reaction. In response to the deterioration, additional ligand, a watersoluble organophosphorus complex ligand, such as TPPTS, is added to the reaction zone at time intervals. Due to the equilibrium reaction with the newly added ligand and with partial displacement of the catalyst poisons from the metal complexes, both the synthesis efficiency and the isomer ratio improve. The hydroformylation is then continued again as usual with the addition of synthesis gas and olefin. However, after repeated additions of the water-soluble organophosphorus complex ligand, the salt and organic load in the catalyst solution is so high that the reaction must be terminated and the entire catalyst solution worked up.

FIG. 2 schematically illustrates the process sequence of the process according to the invention. After a certain process time of the hydroformylation, a partial deactivation of the metal catalysts occurs as in the prior art process, which is noticeable by a deteriorated yield and/or a deteriorated isomer ratio. In this case, a partial amount of the catalyst solution is discharged from the reaction site or reaction system. The discharged portion is replaced with solvent and a diluted catalyst solution is obtained. In addition, the amount of olefin at the reaction site is reduced simultaneously, before or after the discharge. The latter can be achieved, for example, by stopping the olefin feed and allowing the olefin still present in the reaction zone to react out. To the olefin-depleted reaction zone, a rhodium source, and further, water-soluble organophosphorus complex ligands are now added simultaneously or sequentially. This supplemented catalyst solution is preformed to the active catalysts in the absence of olefins and the presence of synthesis gas. After preforming, the olefin feed is restarted and hydroformylation takes place with a much better synthesis efficiency and isomer ratio. In this way, the continuous hydroformylation reaction can be continued consistently over a significantly longer period of time compared to the prior art processes.

EXAMPLES

The advantages of the process according to the invention are illustrated by the following examples.

Example 1 (not According to the Invention, Addition Takes Place in the Presence of Olefin)

A used aqueous catalyst solution (Rh with TPPTS as organophosphorus ligand and a ligand ratio P(III):Rh of about 90:1) was used in a semi-continuous apparatus and operated at 50 bar synthesis gas pressure, 137° C., pH 6.0 and a propylene feed rate of 60 g/h for 14 h. The catalyst was then used for the production of the catalyst. A p-value of 0.272 ($kg_{aldehyde}/L_{catalystsolution} \times h$) is obtained as a measure of catalyst productivity as the initial level. Subsequently, 20% and 35% of the catalyst solution was removed in two steps and replaced with the appropriate amount of deionized water in each case. Although the amount of rhodium at the reaction site was approximately halved by these two partial rejections, the p-value decreased by only about 20%. However, the dilution of the catalyst solution decreased the regioselectivity with respect to the n-aldehyde from 91% to 89%.

The original amount of rhodium in the reactor was then restored by adding rhodium(III) acetate during the ongoing hydroformylation, i.e. adding syngas and feed olefin. The addition of rhodium(III) acetate resulted in a lowering of the P(III):Rh ratio (219 vs. 112 ppm or 74:1 vs. 43:1), although the lowering of the ligand ratio showed no effect on productivity or selectivity. Actually, there should be a significant increase in activity due to the addition of further rhodium. Furthermore, the regioselectivity should decrease further due to the lower P(III):Rh ratio. The following values resulted for the experiment:

TABLE 1

Example 1 - Withdrawal and addition under standard conditions, especially in the presence of olefin. 50 bar, 60 g/h propylene feed, pH 6.0, n-C4-al is calculated as n/(n + i)

| Step | | Vol. [%] | Rh [ppm] | P(III):Rh | T [° C.] | p [kg/L × h] | n-C-al [%]$_4$ |
|---|---|---|---|---|---|---|---|
| 1 | Zero level | — | 223 | 89 | 137 | 0.272 | 90.8 |
| 2 | 1. withdrawal | 20 | 193 | 80 | 137 | 0.240 | 90.9 |
| 3 | 2. withdrawal | 35 | 112 | 75 | 137 | 0.223 | 88.5 |
| 4 | Rh addition | — | 219 | 43 | 137 | 0.224 | 88.5 |

It is clear from the above table that supplementation of the extracted rhodium, without reducing the olefin concentration in the reaction zone, leads only to an insufficient increase in the synthesis efficiency and to no improvement in the n:i isomer ratio. These values also do not improve as a function of time, so this effect cannot be attributed to kinetic effects, such as insufficient time to form the actual active catalyst species. Presumably, the metal introduced as rhodium(III) acetate could not be converted into the catalytically active rhodium(I) complex at all or only to an insufficient extent under the reaction conditions. However, there may also be increased deactivation of the newly added rhodium due to undesirable and competitive complex formation with coordinating ligand degradation products. Under certain circumstances, the added rhodium(III) could form stable rhodium (III)-alkenyl complexes with the olefins present in the reaction zone, which are hydroformylation-inactive and cannot be converted into catalytically active rhodium(I) complexes under the conditions in the reaction zone.

Example 2 (Process According to the Invention, Supplementation in the Absence of Olefins)

At 126° C., 50 bar, a propylene feed of 60 g/h and a pH of 6.0, the basic performance of the used catalyst solution was determined over approx. 23 h with p=0.155 ($kg_{aldehyde}/L_{catalystsolution} \times h$). and 90.9% n-aldehyde content. Subsequently, 21% of the catalyst solution was removed and the volume loss was made up with water. The p-value decreased to 0.138 ($kg_{aldehyde}/L_{catalystsolution} \times h$) and the n-aldehyde percentage to 90.0%. After 36 h, the system was depressurized to 10 bar and then a pressure of 50 bar was adjusted with syngas, removing the propylene present in the reactor. Rhodium(III) acetate was added according to the amount of catalyst previously removed and the catalyst solution was stirred for 3 h at 50 bar synthesis gas pressure as well as 121° C. Subsequently, the propylene addition was restarted. After this procedure, a significantly increased p-value of 0.169 ($kg_{aldehyde}/L_{catalystsolution} \times h$) was obtained. This value for the synthesis performance is above those of the initial level and is high for a used and refreshed catalyst at 126° C. The p-value allows an indication of the amount of product obtained per catalyst volume and time. However, the selectivity decreased to 89.8% n-aldehyde. After 48 h, the ligand TPPTS was added to the system to increase the P(III):Rh to a ratio of >90:1. The volume introduced by the TPPTS resulted in a strong dilution of the catalyst cycle and correspondingly of the rhodium concentration, leading to a decrease of p-value to p=0.130 ($kg_{aldehyde}/L_{catalystsolution} \times h$). However, when dilution is taken into account, a significantly more active catalyst is obtained compared to Example 1. The selectivity also increased to n-portion of 90.7%. Thus, the absence of propylene during addition seems to be crucial for effective rhodium(III) addition, since, in contrast to Example 1, higher productivity and an improved isomer ratio are obtained after addition. In addition, the temperature can be lowered again after supplementation, which can again increase the catalyst lifetime in the further course of the process.

TABLE 2

Example 2-Withdrawal and addition under modified conditions;
50 bar, 60 g/h propylene feed, pH 6.0, n-C4-al is calculated as n/(n + i).

| Step | | Vol. [%] | Rh [ppm] | P(III):Rh | T [° C.] | p [kg/L × h] | n-C4-al [%] |
|---|---|---|---|---|---|---|---|
| 1 | Zero level | — | 293 | 36 | 126 | 0.155 | 90.9 |
| 2 | Withdrawal | 21 | 224 | 36 | 126 | 0.138 | 90.0 |
| 3 | Rh addition | — | 284 | 15 | 126 | 0.169 | 89.8 |
| 4 | TPPTS addition | — | 256 | 120 | 126 | 0.130 | 90.7 |

Example 3 (According to the Invention)

The procedure described in Example 2 was repeated four times in another experiment at 50 bar, 126° C., 140 g/h propylene feed and pH 6. The addition of the new catalyst solution was always carried out in the absence of reactant olefin. The hydroformylation baseline was determined to be p=0.166 ($kg_{aldehyde}/L_{catalystsolution} \times h$) and 92.5% n-C4-al. The activity of the catalyst solution exceeded the baseline level after supplementation of the removed catalyst volume and increased to p=0.178 ($kg_{aldehyde}/L_{catalystsolution} \times h$) on average. The regioselectivity decreased after the 3rd sequence to 90.6% n-content at P(III):Rh of 60:1 and was increased in the 4th sequence by further ligand addition to a ratio of 80:1, which gave a selectivity of 91.1%.

TABLE 3.1

Withdrawal and addition under fully continuous conditions, preforming in
reactor 3 h, 50 bar, 140 g/h propylene feed, pH 6.0, n-C4-al is calculated as n/(n + i)

| Step | | Vol. [%] | Rh [ppm] | P(III):Rh | T [° C.] | p [kg/L × h] | n-C4-al [%] |
|---|---|---|---|---|---|---|---|
| 1 | Zero level | — | 245 | 88 | 126 | 0.166 | 92.5 |
| 2 | Sequence 1 | 20 | 236 | 82 | 126 | 0.179 | 91.6 |
| 3 | Sequence 2 | 20 | 218 | 72 | 126 | 0.180 | 91.1 |
| 4 | Sequence 3 | 20 | 210 | 60 | 126 | 0.176 | 90.6 |
| 5 | Sequence 4 | 20 | 235 | 80 | 126 | 0.178 | 91.1 |

Since the partial substitution aims to increase the activity of the catalyst solution used by discharging deactivating components, the concentrations of corresponding decomposition products were also monitored (Table 3.2). Before the first catalyst removal, the concentrations of TPPOTS were 4.4% and one of the ligand decomposition products (K5) was 7.9%. Thus, the decomposition products include all those organic compounds in the reaction solution which have at least part of the backbone of the organic ligand used and have been chemically modified, at least in part, via the chemical conditions prevailing in the reaction zone. The chemical modifications of the ligands used may include, for example, one or more oxidation/reduction processes and cleavage of one or more functional or CH groups.

The total salt content of the catalyst solution, measured by HPLC analysis, was 29.1%. After the first substitution sequence including the rhodium and TPPTS supplementation, the concentrations of TPPOTS were 3.5% and of K5 6.1%. The total salt content was 23.2% and in this respect significantly lower than the initial level. TPPTS content was 9.8% by supplementation compared to 11.8% previously.

TABLE 3.2

Example 3—Change in salinity after catalyst substitutions.

| Entry | Salt | Start | 1. | Δ [%] | 2. | Δ [%] | 3. | Δ [%] | 4. | Δ [%] |
|---|---|---|---|---|---|---|---|---|---|---|
| 1 | OTS | 4.4 | 3.5 | −20.5 | 3.1 | −11.4 | 2.3 | −25.2 | 1.8 | −21.8 |
| 2 | K5 | 7.9 | 6.1 | −22.8 | 5.7 | −6.6 | 4.7 | −17.6 | 4.0 | −14.9 |
| 3 | TS | 11.8 | 9.8 | −16.9 | 9.3 | −5.1 | 7.2 | −22.6 | 8.1 | +12.5 |
| 4 | Ges. | 29.1 | 23.2 | −20.3 | 21.7 | −6.5 | 17.1 | −21.2 | 16.4 | −4.1 |

Overall, the concentrations of the salts could be reduced by >20% in the first substitution. The TPPTS content, on the other hand, was kept relatively stable by the additions. For the data, it should be noted that the P(III) decomposition was not balanced during the first substitution sequences. Only in the last sequence was a significant excess of TPPTS added, bringing the TPPTS content to 12.5% or a P(III):Rh ratio of >80:1.

Example 4 (Combining the Individual Metal Sources and Ligand Addition)

In this experiment, at 139° C., 50 bar, a propylene feed of 145 g/h and a pH of 6.0, the activity and selectivity decrease of a catalyst solution was monitored for 427 h, which had a very low P(III):Rh ratio of <50:1. The p-value decreased steadily within the reaction time from 0.237 ($kg_{aldehyde}/L_{catalystsolution} \times h$) to 0.123 ($kg_{aldehyde}/L_{catalystsolution} \times h$). Substitution of 20% of the catalyst volume was then initiated. The propylene feed was stopped, the propylene in the reactor was converted and 20% of the catalyst volume was removed from the catalyst loop. The missing catalyst volume was directly replaced with an appropriate amount of rhodium(III) acetate dissolved in an aqueous TPPTS solution (about 30 wt. %; resulting in P(III):Rh=102:1). At reaction temperature (138° C.) and under a syngas atmosphere (50 bar), the approximately propylene-free reaction mixture was stirred for 3 h before propylene feed was then started slowly and increased up to 145 g/h. In the first 20 h after the substitution, the p-value increased from 0.123 ($kg_{aldehyde}/L_{catalystsolution} \times h$) to 0.184 ($kg_{aldehyde}/L_{catalystsolution} \times h$) and further to 0.209 ($kg_{aldehyde}/L_{catalystsolution} \times h$) in the following 24 h. The p-value of the reaction mixture was then increased to 0.1. Moreover, since the substitution here was carried out in one step, i.e., by simultaneous addition of the rhodium source in a solution with or with simultaneous addition of ligands, prior stabilization of the catalyst solution by TPPTS was not required. The results of this sequence are as follows:

TABLE 4

Substitution on an inactive catalyst solution (fully continuous).
50 bar, 145 g/h propylene feed, pH 6.0, n-C4-al is calculated as n/(n + i)

| Step | | Vol. [%] | Rh [ppm] | P(III):Rh | T [° C.] | p [kg/L × h] | n-C4-al [%] |
|---|---|---|---|---|---|---|---|
| 1 | Start | — | 271 | 44 | 139 | 0.234 | 89.5 |
| 2 | End | — | 274 | 28 | 139 | 0.123 | 89.8 |
| 5 | Supplement | 20 | 268 | 99 | 139 | 0.209 | 89.0 |

Example 5 (Aged Catalyst Solution)

In a preferred process variant, an attempt was made to carry out the substitution sequence on a very strongly aged catalyst solution. At 50 bar, 138° C., 140 g/h propylene input and a pH of 6.0, the base level of the reaction was determined and the substitution sequence was started with withdrawal and dilution. At this point, the hydroformylation broke down and the experiment had to be terminated. A reactivation of the catalyst was not possible.

TABLE 5

Example 5 - Substitution on an inactive catalyst solution (fully continuous). 50 bar, 140 g/h propylene feed, pH 6.0, n-C4-al is calculated as n/(n + i)

| Step | | Vol. [%] | Rh [ppm] | P(III):Rh | T [° C.] | p [kg/L × h] | n-C4-al [%] |
|---|---|---|---|---|---|---|---|
| 1 | Zero level | — | 247 | 42 | 138 | 0.147 | 90.2 |
| 2 | Withdrawal | 20 | 185 | 35 | 138 | 0.078 | 90.2 |

If a very aged catalyst solution already has a low ligand to rhodium ratio, substitution of the metal alone will not reactivate the catalyst solution. In these cases, the ligands are the determining factor and not the metal. Nevertheless, reactivation can be achieved via the process of the invention. A possible process for these cases is given in Example 6.

Example 6 (Aged Catalyst Solution)

Under modified conditions, additional ligand was first added to the catalyst solution used in Example 5 to stabilize the system (50 bar, 136° C., 40 g/h propylene input, pH of 6.0). Already by the addition of ligand alone, a clear increase in activity as well as selectivity was observed, which proves that the ligand concentration is the determining factor for the productivity of the catalyst. After stabilization by ligand addition, the substitution sequence according to the invention was carried out twice, the preforming time being 3 h in each case. The decrease of the temperature from 136° C. to 131° C. after stabilization as well as the respective possible increase of the olefin input after the substitutions (40 g/h→45 g/h→55 g/h) are signs of a clear catalyst activity increase. The result shows that very inactive catalyst solutions can also be subjected to substitution and reactivation. For this purpose, however, these special catalyst solutions must first be stabilized by further ligand addition. The results of the substitution are shown in Table 6.

TABLE 6

Example 6 - Substitution on an inactive catalyst solution after prior stabilisation (fully continuous), n-C4-al is calculated as n/(n + i)

| Step | | Vol. [%] | Rh [ppm] | P(III):Rh | Propylene-input [g/h] | T [° C.] | p [kg/L × h] | n- C4-al [%] |
|---|---|---|---|---|---|---|---|---|
| 1 | Zero level | — | 253 | 46 | 40 | 136 | 0.162 | 87.7 |
| 2 | Stabilization | — | 236 | 67 | 40 | 136 | 0.197 | 90.9 |
| 3 | Stabilization | — | 236 | 67 | 40 | 131 | 0.145 | 90.9 |
| 4 | Sequence 1 | 20 | 248 | 57 | 45 | 131 | 0.163 | 90.2 |
| 5 | Sequence 2 | 20 | 240 | >42 | 55 | 131 | 0.158 | 90.9 |

The invention claimed is:

1. A continuous two-phase hydroformylation process for the production of aldehydes from olefins by means of carbon monoxide, hydrogen and a transition metal catalyst in a reaction zone, the transition metal being in the form of a water-soluble catalyst complex, characterised in that the process comprises the following steps once or several times:
   a) hydroformylating by reacting the olefins, carbon monoxide and hydrogen over a water-soluble transition metal catalyst comprising water-soluble organophosphorus ligands in the reaction zone;
   b) reducing the concentration of the olefins in the reaction zone by reducing the olefin feed to the reaction zone by greater than or equal to 50% and less than or equal to 100% based on the concentration of olefin in the reaction zone in process step a) and withdrawing at least a portion of the catalyst solution from the reaction system, wherein the catalyst solution withdrawal and olefin concentration reduction substeps may occur in this or reverse order, simultaneously or sequentially;
   c) feeding a solvent, a transition metal source and water-soluble organophosphorus ligands to the reaction system, wherein the feeding of the components may occur simultaneously or in any order sequentially;
   d) increasing the concentration of the olefins in the reaction zone by increasing the olefin feed to the reaction zone and hydroformylating by reacting the olefins with carbon monoxide and hydrogen.

2. The process according to claim 1, wherein in process step b) the sub-step of reducing the olefin concentration occurs prior to the partial withdrawal of the catalyst solution.

3. The process according to claim 1, wherein in process step b) a volume greater than or equal to 10% and less than or equal to 50% of aqueous catalyst solution is removed from the reaction system.

4. The process according to claim 1, wherein the volume of liquid components added in process step c) is greater than or equal to 20% and less than or equal to 200% relative to the catalyst solution removed in process step b).

5. The process according to claim 1, wherein in process step c), as transition metal source, rhodium compounds are selected from the group of rhodium (III) salts comprising Rh-2-ethylhexanoate, -acetate, -oxalate, -propionate, -malonate, $Rh(NO_3)_3$, $Rh(SO_4)_3$, $RhCl_3$ or the rhodium complex compounds, selected from the group consisting of cyclopentadienylrhodium compounds, $[RhCl(cyclooctadiene-1,5)]_2$, rhodium acetylacetonate, or the rhodium carbonyl compounds selected from the group consisting of $Rh_3(CO)_{12}$, $Rh_6(CO)_{16}$.

6. The process according to claim 1, wherein in process step c) preformed rhodium complexes with organophosphorus ligands are added to the reaction system as a transition metal source.

7. The process according to claim 1, wherein in process step c) organophosphorus ligands are added in a molar ratio of greater than or equal to 20 and less than or equal to 400 relative to the amount of transition metal removed in process step b).

8. The process according to claim 1, wherein in process step c) a solution of a rhodium compound comprising organophosphorus ligands is fed to the reaction system.

9. The process according to claim 1, wherein in process step c) organophosphorus ligands are added to the reaction system prior to addition of the transition metal source.

10. The process according to claim 1, wherein in process step c), first a partial amount of the solvent, then the transition metal source dissolved in a solvent, and then the organophosphorus ligands are fed to the reaction system.

11. The process according to claim 1, wherein by process steps b) and c) the total concentration of organic ligands and salts present in the aqueous solution of the reaction zone are reduced by greater than or equal to 10% and less than or equal to 50% compared to the concentration of organic ligands and salts in the aqueous solution of the reaction zone at the end of process step a).

12. The process according to claim 1, wherein in process step c) the pH in the aqueous solution of the reaction zone is adjusted to a range of greater than or equal to pH 4 and less than or equal to pH 10.

13. The process according to claim 1, wherein the molar ratio of added organophosphorus ligands to added rhodium in process step c) is greater than or equal to 20 and less than or equal to 500.

14. The process according to claim 1, wherein by process steps b) and c) the concentration of inorganic cations in the reaction zone solution is reduced by greater than or equal to 5%.

15. The process according to claim 2, wherein in process step b) the molar concentration of olefin in the reaction zone is reduced by greater than or equal to 50% and less than or equal to 100% based on the concentration of olefin in the reaction zone in process step a).

16. The process according to claim 2, wherein in process step b) a volume greater than or equal to 10% and less than or equal to 50% of aqueous catalyst solution is removed from the reaction system.

17. The process according to claim 2, wherein the volume of liquid components added in process step c) is greater than or equal to 20% and less than or equal to 200% relative to the catalyst solution removed in process step b).

18. The process according to claim 2, wherein in process step c), as transition metal source, rhodium compounds are selected from the group of rhodium (III) salts comprising Rh-2-ethylhexanoate, -acetate, -oxalate, -propionate, -malonate, $Rh(NO_3)_3$, $Rh(SO_4)_3$, $RhCl_3$ or the rhodium complex compounds selected from the group consisting of cyclopentadienylrhodium compounds, $[RhCl(cyclooctadiene-1,5)]_2$, rhodium acetylacetonate, or the rhodium carbonyl compounds selected from the group consisting of $Rh_3(CO)_{12}$, $Rh_6(CO)_{16}$.

19. The process according to claim 2, wherein in process step c) preformed rhodium complexes with organophosphorus ligands are added to the reaction system as a transition metal source.

* * * * *